(12) United States Patent
Carmen et al.

(10) Patent No.: US 11,221,100 B1
(45) Date of Patent: Jan. 11, 2022

(54) PROTECTIVE COVER FOR OXYGEN LINES

(71) Applicants: Gary Carmen, Finlayville, PA (US); Joan Carmen, Finlayville, PA (US)

(72) Inventors: Gary Carmen, Finlayville, PA (US); Joan Carmen, Finlayville, PA (US)

( * ) Notice: Subject to any disclaimer, the term of this patent is extended or adjusted under 35 U.S.C. 154(b) by 0 days.

(21) Appl. No.: 16/841,902

(22) Filed: Apr. 7, 2020

(51) Int. Cl.
*F16L 57/06* (2006.01)
*F16L 57/02* (2006.01)

(52) U.S. Cl.
CPC .............. *F16L 57/02* (2013.01); *F16L 57/06* (2013.01)

(58) Field of Classification Search
CPC . F16L 57/00; F16L 57/02; F16L 57/06; F21V 33/00; F21V 21/08; F21S 4/00
USPC ....... 138/110, 115, 116, 156, 163, 128, 121; 362/253, 396, 555, 572, 391, 84, 96; 174/72 A, 68.3, 68.1
See application file for complete search history.

(56) References Cited

U.S. PATENT DOCUMENTS

| | | | | |
|---|---|---|---|---|
| 3,060,069 | A * | 10/1962 | Sindars | F16L 59/022 138/120 |
| 4,384,167 | A * | 5/1983 | Nestor | H02G 3/0468 174/135 |
| 4,899,414 | A * | 2/1990 | Irwin | A47L 11/40 138/110 |
| 6,491,067 | B1 * | 12/2002 | Davenport | F16L 7/00 138/110 |
| 6,774,312 | B2 * | 8/2004 | Fatato | F16L 3/26 138/122 |
| 7,045,708 | B2 * | 5/2006 | Miura | F16B 21/088 174/50 |
| 7,374,318 | B2 * | 5/2008 | Brooks | A61M 16/08 362/191 |
| 7,781,674 | B2 * | 8/2010 | Kassab | H02G 3/0481 174/36 |
| 2003/0189492 | A1 | 10/2003 | Harvie | |
| 2004/0200536 | A1 * | 10/2004 | Strasser | A62C 33/00 138/104 |
| 2006/0174877 | A1 | 8/2006 | Jagger | |
| 2010/0157584 | A1 * | 6/2010 | Ho | F21S 4/00 362/223 |
| 2015/0075528 | A1 * | 3/2015 | Kudo | A61M 16/0875 128/204.18 |
| 2015/0165154 | A1 * | 6/2015 | Watchous | F21V 33/0068 362/253 |

* cited by examiner

*Primary Examiner* — Patrick F Brinson
(74) *Attorney, Agent, or Firm* — Sanchelima & Associates, P.A.; Christian Sanchelima; Jesus Sanchelima

(57) ABSTRACT

A system for a protective cover including a cover assembly and a light assembly. The cover assembly includes a cover that has a slit. The slit allows retrofitting any existing oxygen lines with the cover in order to provide protection to the oxygen lines. This helps to prolong the lifespan of the oxygen lines. Further, the light assembly may include a plurality of lights. The lights are mounted to the cover in order to illuminate a surrounding area. This helps to reduce the chances that anyone trips, falls or gets injured due to the oxygen lines. The user benefits from increased safety as there are less chances that their oxygen supply is cutoff from an oxygen line becoming damaged. The oxygen lines are kept in working order for a prolonged period of time. The lights are controlled either locally or remotely, as well as manually or automatically.

13 Claims, 3 Drawing Sheets

PROTECTIVE COVER FOR OXYGEN LINES

BACKGROUND OF THE INVENTION

1. Field of the Invention

The present invention relates to a protective cover and, more particularly, to a protective cover for oxygen lines that protects the oxygen lines from damage to avoid frequent replacing thereof. Further, the protective cover includes a plurality of lights making locating of the oxygen line quick and easy.

2. Description of the Related Art

Several designs for protective covers for oxygen lines have been designed in the past. None of them, however, include a protective covering which acts not only as lighting to prevent falls or trips, but also as damage protection to ensure the oxygen line remains in working order. Tripping on the oxygen lines may lead to the person who tripped to get seriously injured. This makes reducing the chances of a tripping accident occurring crucial, especially for the elderly. Oxygen lines may need to be protected from damage from pets, for example. This can be deadly as some users may need a constant supply of oxygen, which is why it is essential to keep the oxygen lines functioning properly at all times.

Applicant believes that a related reference corresponds to U.S. patent publication No. 2003/0189492 for a monitoring, alarm and automatic adjustment system for users of oxygen and compressed air. Applicant believes another related reference corresponds to U.S. patent publication No. 2006/0174877 for a portable oxygen concentrator with a docking station. None of these, however, teach of a cover for oxygen lines that protects the oxygen lines from damage to ensure they are functioning properly. Further, the cover can be illuminated to reduce the chances of someone tripping over the oxygen lines and potentially injuring themselves and damaging the oxygen lines. The cover is also less complex than the existing art.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a protective cover that protects oxygen lines from damage.

It is another object of this invention to provide a protective cover that reduces the amount of times that oxygen lines need replacing.

It is still another object of the present invention to provide a protective cover that increases the safety of the user by ensuring that the oxygen lines are in functioning order so that the needed oxygen supply is always being administered.

It is another object of this invention to provide a protective cover that illuminates to reduces the chances of a person or user tripping on the oxygen lines, which also helps to increase the safety of the user and other persons.

It is still another object of the present invention to provide a protective cover that can be retrofitted onto existing oxygen lines.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
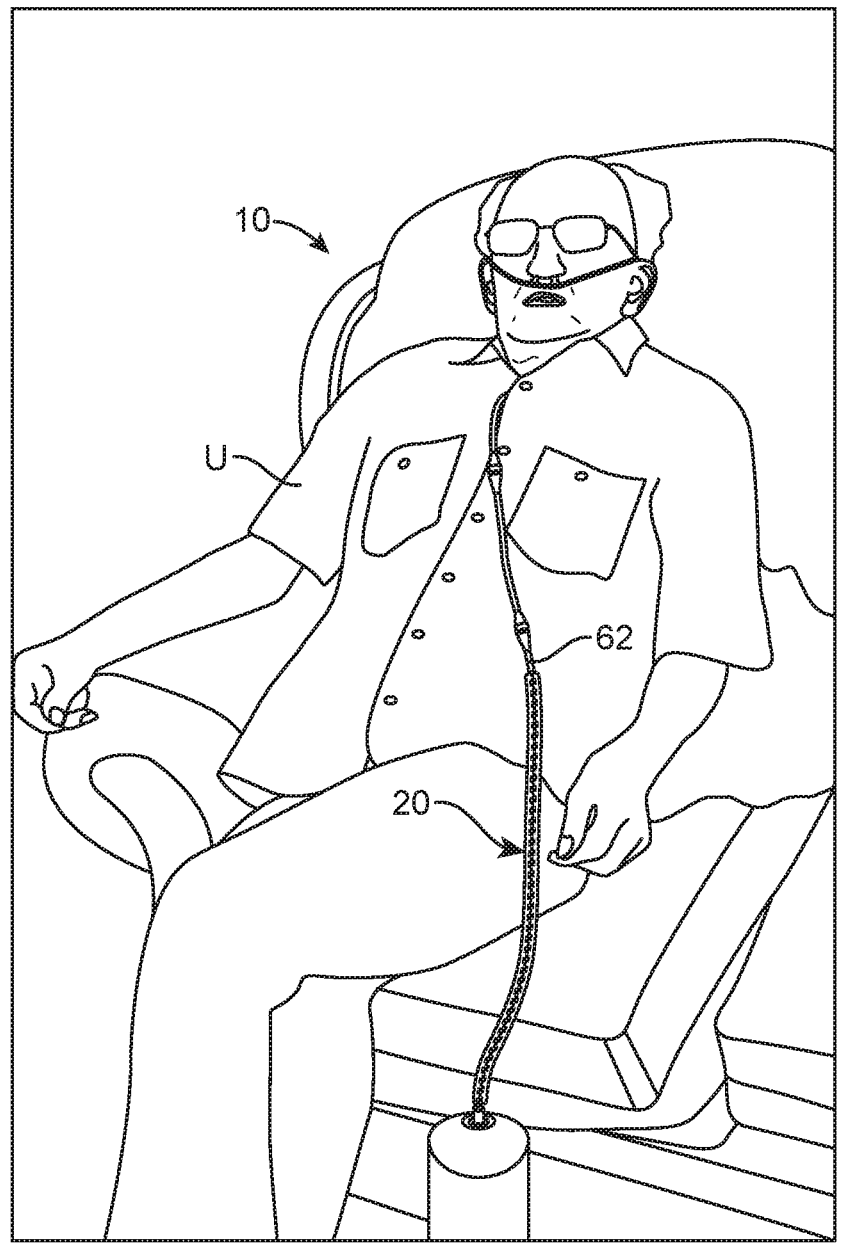
FIG. 1 represents the present invention in an operational setting covering an oxygen line 62.

Referring now to the drawings, where the present invention is generally referred to with numeral 10, it, protective cover 10, can be observed that it basically includes a cover assembly 20 and a light assembly 40.

The present invention provides protection to oxygen lines from pets or other damaging elements. This helps to prolong the life span of the oxygen lines. This serves to increase the safety of the user. Also, to save the user money by reducing the amount of times that it necessary to change damaged oxygen lines. The present invention is further configured to illuminate a surrounding area to avoid having the user trip and fall, which could lead to serious injury.

Figure 2:
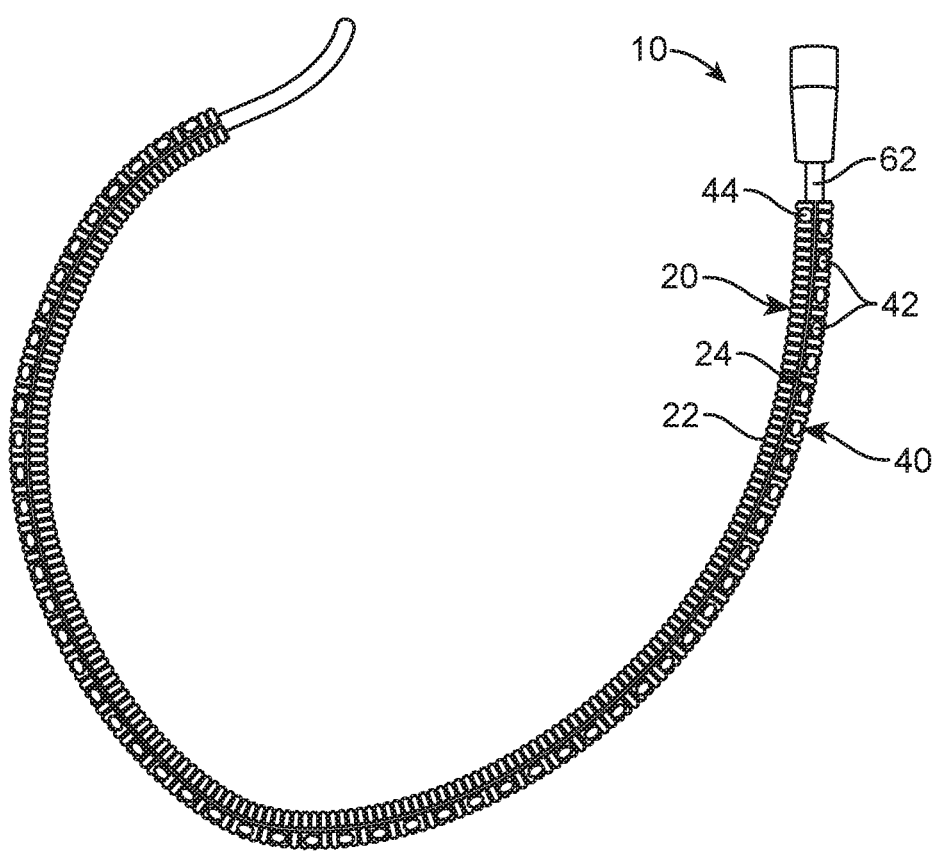
FIG. 2 shows an isometric view of the protective cover 10, in accordance with an embodiment of the present invention in which cover 22 includes ridges.
Figure 3:
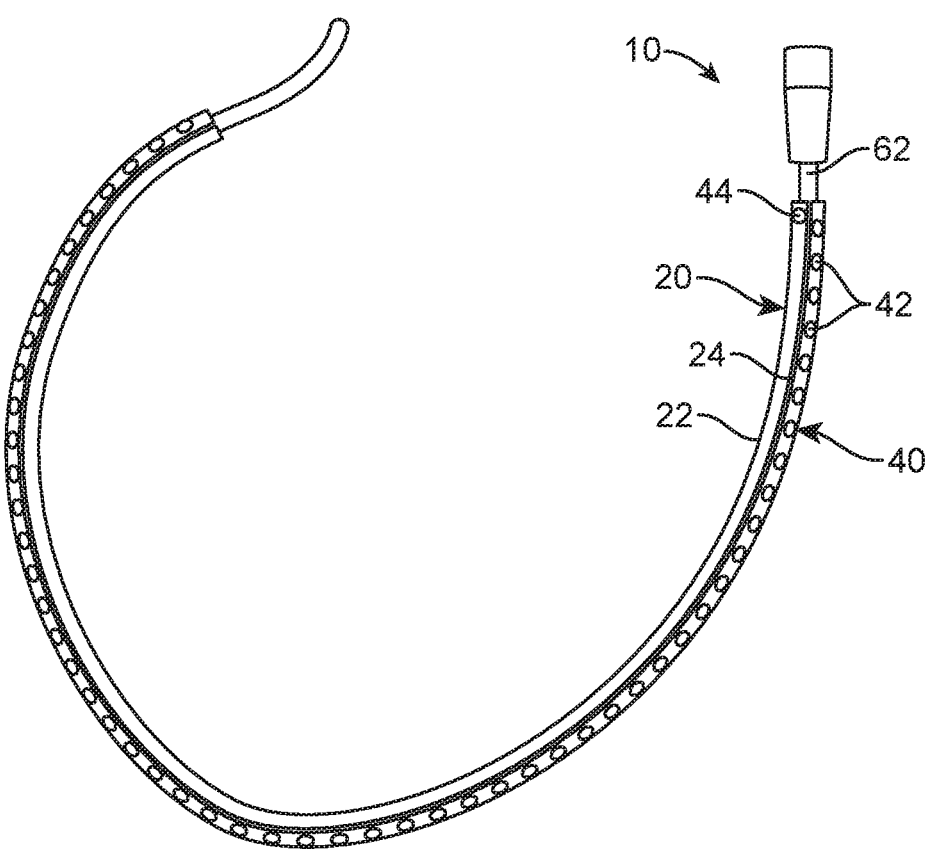
FIG. 3 illustrates an isometric view of the protective cover 10, in accordance with an alternate embodiment of the present invention in which cover 22 is entirely smooth.

Referring to FIG. 1-3, it can be seen that cover assembly 20 may provide essential protection to an oxygen line 62. Cover assembly 20 may include a cover 22. Cover 22 may be a protective covering. Cover 22 may be mounted around oxygen line 62 to provide the necessary protection to oxygen line 62. Oxygen line 62 may be attached to an oxygen supply tank on one end and to a user on an opposite end. It should be understood that cover 22 may be substantially hollow to allow for oxygen line 62 to fit securely within cover 22. Cover 22 may preferably be cylindrical or circular, however, it should be understood that virtually any other shape may be suitable for cover 22. Cover 22 may have a dimension slightly greater than the dimensions of oxygen line 62. Cover 22 may be made of a rigid material to provide ample protection to oxygen line 62. It may also be suitable for cover 22 to be flexible to be able to twist and turn with oxygen line 62, while still being sturdy and strong enough to prevent damage to oxygen line 62. Cover 22 may be made of materials such as rubber, plastic, polymer, metal, carbon fiber or the like. It should be understood that cover 22 may include ridges along an entire length of cover 22 as seen in FIG. 2. In an alternate embodiment, cover 22 may be entirely smooth as seen in FIG. 3. Additionally, it may be suitable for cover 22 to be transparent, semitransparent or opaque as well. In order to accommodate oxygen line 62 and further allow full functionally of oxygen line 62 while within with the present invention, cover 22 may include an opening at each distal end. In one embodiment, oxygen line 62 may extend slightly beyond the length of cover 22. Importantly, cover 22 may include a slit 24 along an entire length thereof. Slit 24 allows for oxygen line 62 to be fitted within cover 22. Slit 24 also further allows for quick and easy removal and retrieval of oxygen line 62. Slit 24 may be a cut along the length of cover 22. It is to be understood that any existing oxygen lines may be retrofitted with cover 22.

Light assembly 40 may be mounted to cover assembly 20 in order to be able to illuminate a surrounding area. Light assembly 40 allows a person to be able to see oxygen line 62, even at night, to avoid tripping and falling over oxygen line 62. Light assembly 40 may include a plurality of lights 42. Preferably, lights 42 may be LED lights. Lights 42 may be mounted to cover 22. Lights 42 may be mounted with fasteners, hook and loop straps, adhesives, buttons, snap buttons or the like as known in the art. Preferably, lights 42 may be mounted within cover 22 if cover 22 is transparent or semitransparent. Lights 42 may preferably be mounted on an outer surface of cover 22 if cover 22 is opaque or solid. Lights 42 may be programmed to turn on and illuminate during predetermined time periods. It may also be suitable for lights 42 to be programmed to be on for a predetermined amount of time before automatically turning off. Lights 42 may emit light of predetermined colors, but preferably white light is emitted by lights 42. Lights 42 may include a switch 44 to manually turn on and off lights as shown in FIG. 2 and FIG. 3. Switch 44 permits the actuating of plurality of lights 42. It may be suitable for switch 44 may be mounted to cover 22 or to lights 42.

In an alternate embodiment, it may be suitable to control lights 42 with a remote or with a mobile application on a mobile phone. Control of lights 42 may include turning on and off of lights 42 with the remote. It may be suitable to control the color of light emitted by light 42. It may be suitable to have the present invention cycle through different colored lights or modes as well or. The remote or mobile application allows the user to control lights 42 even when they are not near the present invention. The remote adds comfort and versatility to the present invention. It is possible to control lights 42 remotely or locally and, as well as, automatically or manually.

The present invention allows for increased safety to the user that use oxygen lines. Importantly, oxygen line 62 is kept in working order which is crucial for some users to maintain a constant flow of oxygen to survive. The present invention further allows the user to save money as there is less of a need to replace damaged oxygen lines.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A system for a protective cover, comprising:
   a. an oxygen line;
   b. a cover assembly including a cover being a protective covering and having a slit extending along a length of the cover, said cover is flexible, said cover is opaque, said cover has a cylindrical shape, said cover is hollow, said cover has ringed ridges, said ringed ridges have a circular shape, each of the ringed ridges is located next to each other, said ringed ridges are located along a surface of the cover, said oxygen line secured within said cover through said slit; and
   c. a light assembly including a plurality of lights mounted along the length of the cover, said plurality of lights are mounted on the ringed ridges of the cover, said plurality of lights emit white light, said plurality of lights are activated by a switch, said switch is located on one of the ringed ridges.

2. The system of claim 1, wherein said cover is made of a ridged material.

3. The system of claim 1, wherein said cover is made of rubber.

4. The system of claim 1, wherein said plurality of lights are LED lights.

5. A system for a protective cover, comprising:
   a. an oxygen line connected to an oxygen supply tank on one end and to a user on an opposite end;
   b. a cover assembly including a cover being a protective covering and having a slit extending along a length of the cover, said cover being flexible and cylindrical, wherein said oxygen line is secured within said cover through said slit, said oxygen line extending beyond distal ends of said cover; and
   c. a light assembly including a plurality of lights mounted along the length of the cover, said plurality of lights being LED lights, said plurality of lights emit white light, said light assembly further including a switch to actuate said plurality of lights.

6. The system of claim 5, wherein said cover includes an outer surface, said outer surface being smooth.

7. The system of claim 6, wherein said outer surface includes ridges along an entire length of said cover.

8. The system of claim 5, wherein said cover is made of rubber.

9. The system of claim 5, wherein said cover is hollow.

10. The system of claim 5, wherein said plurality of lights have oval shape.

11. The system of claim 1, wherein each of the ringed ridges have the same size.

12. The system of claim 1, wherein said plurality of lights are located next to the slit.

13. A system for a protective cover, consisting of:
   d. an oxygen line connected to an oxygen supply tank on one end and to a user on an opposite end;
   e. a cover assembly including a cover being a protective covering and having a slit extending along a length of the cover, said cover being flexible and cylindrical, said cover is opaque, said cover is hollow, said cover is made of rubber, said cover includes ringed ridges along surface of the cover, each of the ringed ridges has a circular shape, each of the ringed ridges has the same size, each of said ringed ridges is next to each other, said oxygen line is secured within said cover through said slit, each of the distal ends having an opening, said oxygen line extending beyond distal ends of said cover; and
   f. a light assembly including a plurality of lights mounted on the ringed ridges of cover, said plurality of lights are located along the length of the cover, said plurality of lights are located next to the slit, said plurality of lights are located on the ringed ridges, the plurality of lights are equally spaced, said plurality of lights being LED lights, said plurality of lights emit white light, said plurality of lights have oval shape, said plurality of lights are activated by a switch, said switch is located on a ridge of a distal end of said cover, said switch has a circular shape.

* * * * *